United States Patent [19]

Chakrabarty et al.

[11] Patent Number: 4,535,061
[45] Date of Patent: Aug. 13, 1985

[54] BACTERIA CAPABLE OF DISSIMILATION OF ENVIRONMENTALLY PERSISTENT CHEMICAL COMPOUNDS

[75] Inventors: Ananda M. Chakrabarty, Villa Park, Ill.; Scott T. Kellogg, Gaithersburg, Md.

[73] Assignee: University of Illinois Foundation, Urbana, Ill.

[21] Appl. No.: 334,519

[22] Filed: Dec. 28, 1981

[51] Int. Cl.$^3$ .................. C12N 1/20; C12N 15/00; C02F 3/00
[52] U.S. Cl. ............................ 435/253; 435/172.1; 435/262; 435/874; 435/830; 210/601
[58] Field of Search ................. 435/172, 253, 172.1

[56] References Cited

U.S. PATENT DOCUMENTS 4,259,444  3/1981  Chakrabarty .

OTHER PUBLICATIONS

Sakaguchi et al., Molecular Breeding and Genetics of Applied Microorganisms pp. 47–60 (Jan. 1981).
Kamp et al., Plasmids of Medical Environmental and Commercial Importance pp. 275–285, (1979).
Pint Principles of Microbe and Cell Cultivation, pp. 42–56, (1975).
Chatterjee, et al., pp. 519–528 in "Molecular Biology, Pathogenicity and Ecology of Bacterial Plasmids" (Levy et al., eds.), Plenum Pub. Corp., N.Y. (1981).
Don, et al., J. Bacteriol., 145: 681–686, (1981).
Fisher, et al., J. Bacteriol., 135: 798–804, (1978).
Furukawa, et al., Appl. Environ. Microbiol., 38: 301–311, (1979).
Furukawa, et al., Agric. Biol. Chem., 43, pp. 1577–1583, (1979).
Hartman, et al., Appl. Environ. Microbiol., 37: 421–428, (1979).
Horvath, Bull. Environ. Contam. Toxicol., 5: 537–541, (1971).
Kawasaki, et al., Agric. Biol. Chem., 45: 1477–1481, (1981).
Novick, et al., PNAS, 36: 708–719, (1950).
Novick, et al., Science, 112: 715–716, (1950).
Monod, Ann. Inst. Pasteur., 79: 390–410, (1950).
Myers, et al., J. Gen. Physiol., 28: 103–112 (1944).
Perry, Microbiol. Rev., 43: 59–72, (1979).
Reineke, et al., J. Bacteriol., 142: 467–473, (1980).
Rosenberg, et al., J. Agric. Food. Chem., 28: 705–709, (1980).
Slater, et al., J. Gen. Microbiol., 114: 125–136, (1979).
Alexander, Science, 211: 132–138, (1981).
Chakrabarty, Ann. Rev. Gen., 10: 7–30, (1976).
Chatterjee, et al., J. Bacteriol., 146: 639–646, (1981).
Monod, Ann. Inst. Pasteur., 79: 390–410, (1950)—English-language translation.

Primary Examiner—Alvin E. Tanenholtz
Attorney, Agent, or Firm—Marshall, O'Toole, Gerstein, Murray, & Bicknell

[57] ABSTRACT

Plasmid-assisted molecular breeding procedures for generating pure and mixed cultures of microorganisms capable of dissimilating environmentally persistent chemical compounds. Continuously cultured growth of microorganisms is carried out in the presence of a source of DNA plasmids participative in dissimilation of compounds structurally analogous to the persistent compounds and under chemostatic conditions including gradually increasing concentrations of the persistent compound. Novel microorganism products of the procedures include a mixed Arthrobacter and Pseudomonas culture, A.T.C.C. 39028, capable of total degradation of mixed polychlorinated biphenyls (e.g., Arochlor 1221) and a pure culture of Pseudomonas cepacia, A.T.C.C. 39027, which can utilize 2,4,5-trichlorophenoxyacetic acid (2,4,5-T) as its sole carbon source. Disclosed also are procedures for using pure and mixed cultures of the invention in degrading persistent compounds contaminating soil and aqueous environments.

2 Claims, No Drawings

BACTERIA CAPABLE OF DISSIMILATION OF ENVIRONMENTALLY PERSISTENT CHEMICAL COMPOUNDS

BACKGROUND

The present invention relates to microbial genetic engineering practiced with the goal of developing new strains of microorganisms which are capable of dissimilating environmentally persistent chemical compounds.

Over the past several decades, numerous synthetic chemical compounds have been released into the environment in the form of insecticides, herbicides, propellants, lubricants, plasticizers, refrigerants, fire retardants and the like, with resultant accumulation of the compounds in the biosphere. In addition to commercially used synthetic compounds, large quantities of "waste" chemicals are formed during and after manufacture of synthetic compounds and have been stored by the chemical industry at waste dump sites. Production levels of synthetic organic chemicals have doubled every seven or eight years for the past three decades and annual production now exceeds 175,000,000 pounds per year.

Among the most widely used products of organic synthesis are the halogenated compounds. The introduction of halogen atoms (fluorine, chlorine, bromine, iodine) into organic molecules will frequently render them highly toxic to many insects, pests, weeds and pathogenic microorganisms. Such toxicity factors, coupled with relative ease of bulk synthesis, have made halogenated organic compounds, especially chlorinated aromatic compounds, highly desirable as herbicides and insecticides. Indeed, these compounds have been successfully used on a worldwide basis in concerted programs for the enhancement of agricultural productivity and elimination of insect vectors for transmission of disease.

The persistence of halogenated compounds in the environment for long periods after application was initially seen as a significant advantage. Most naturally-occurring microorganisms in soil and water simply do not possess the enzymatic capability for dissimilation of halogenated compounds (probably owing to the rarity of natural analogs of such compounds and the consequent absence of significant selective pressures favoring such capabilities). Because the compounds persisted in soil and water without being subjected to microbial degradation, repeated application of the herbicides and pesticides was not necessary.

Many halogenated aromatic compounds are lipophilic and not readily soluble in water. Herbicide and pesticide residues ingested by animals therefore tended to accumulate in fatty tissues, eventually making their way into the human food chain where they can have toxic, mutagenic and potentially carcinogenic effects. In addition to the gradual entry of such compounds into the food chain, humans have been subjected to hazard by the accidental release of large quantities of toxic compounds at manufacturing and storage facilities and along transportation routes. Pollution problems of tragic proportion in terms of human suffering and property damage have resulted from the well known episodes at Love Canal, NY, Seveso, Italy, and Yusho, Japan. Exposure of humans to high concentrations of persistent toxic compounds has also resulted from deliberate use of huge quantities of chlorinated aromatic hydrocarbons as defoliants in warfare. Finally, there are more than 3500 known waste dump sites in the United States alone where hazardous chemicals have been buried over the past decades and many of the dumps provide a potential or actual source of contamination of surface and ground waters near population centers.

The effective removal of environmentally persistent chemicals thus constitutes a problem of the highest order on a worldwide basis, with "target" compounds including: chlorinated dibenzo-p-dioxins (which are among the most highly toxic compounds known to man); 2,4,5-trichlorophenoxy acetic acid ("2,4,5-T", an Agent Orange constituent believed to include dioxins as manufacturing impurities and to generate dioxins upon combustion); chlorophenols; the mixed polychlorinated biphenyls ("PCB's"); lignin (in biomass conversion systems) and highly viscous recalcitrant components of oil (in secondary oil recovery systems). At present, there are few methods for dealing with contaminated industrial and municipal sludges or soils. It is possible to destroy most liquid toxic wastes completely with special high temperature/high oxygen incineration processing, but there is no easy disposal method available for contaminated soil or heavy sludges other than containment or burial.

Certain highly chlorinated compounds do appear to be metabolized by soil microorganisms by a mechanism known as co-oxidation. [See, e.g., Perry, *Microbiol. Rev.*, 43, pp. 59–72 (1979).] Under co-oxidation conditions, the compounds are acted upon by individual members of the total microfloral population, each performing only a partial conversion of the substrate. The co-oxidation of a number of persistent chlorinated compounds such as 2,4,5-trichlorophenoxy acetic acid (2,4,5-T), 1,1-bis(p-chlorophenyl)-2,2,2'-trichloroethane (DDT) and [2-(2,4,5-trichlorophenoxy) propionic acid (Silvex) by mixed cultures is thus well known. Because individual microorganisms performing partial conversions rarely obtain energy from the conversion process, the entire conversion process is exceedingly slow and dependent upon the presence of other metabolizable carbon sources in the environment. Recent extensive studies of co-metabolizing mixed cultures capable of degrading, e.g., 2,4,5-T, reveal that co-oxidation processes can lead to chloride release, formation of phenolic products and/or cleavage of the armoatic ring, but that none of the microorganisms involved grow by using the herbicides as a sole carbon and/or energy source. See, e.g. Rosenberg, et al., *J. Agric. Food. Chem.*, 28, pp. 705–709(1980) and Alexander, *Science*, 211, pp. 132–138 (1981).

While highly chlorinated compounds are recalcitrant to microbial attack except by co-oxidation, many simple halogenated compounds have been found to be susceptible to dissimilation by means of microbial degradation. Pure cultures have been isolated which are able to use mono-and di-chlorinated compounds such as 4-chlorobiphenyl, 3-chlorobenzoic acid, 2,4-dichlorophenoxyacetic acid and various fluoro- and chloroacetates and propionates. See, e.g., Kamp, et al., at pp. 97–109. In "Plasmids of Medical, Environmental and Commercial Importance" Timmis, et al. (eds.) Elsevier/North-Holland Biomedical Press, Amsterdam (1979); Reineke, et al., *J. Bacteriol.*, 142, pp. 467–473 (1980); Chatterjee, et al., *J. Bacteriol.*, 146, pp. 639–646 (1981); Don, et al. *J. Bacteriol.*, 145, pp. 681–686 (1981); Slater, et al., *J. Gen. Microbiol.*, 114, pp. 125–136 (1979); and, Kawasaki, et al., *Agric. Biol. Chem.*, 45, pp. 1477–1481 (1981).

As in the case of petroleum degradative organisms (see, e.g., co-inventor Chakrabarty's U.S. Pat. No. 4,259,444), in many instances the degradative enzymes needed for microorganisms to dissimilate simple halogenated compounds are coded for by genes borne on DNA plasmids. While a single plasmid generally appears to encode only a single degradative pathway, plasmids often interact to greatly extend the number of xenobiotic compounds that can be degraded by a pure culture. An example of such interaction with regard to chlorinated aromatic compounds is found in the case of *Pseudomonas* species B-13 [see, Hartman, et al., *Appl. Environ. Microbiol.*, 37, pp. 421–428 (1979)]. This strain, which could utilize 3-chlorobenzoate as a sole source of carbon, was subjected to introduction of the toluene oxygenase, "TOL", plasmid and it was thereafter possible to select variants of the strain which could also utilize 4-chlorobenzoic acid or 3,5-dichlorobenzoic acid as a carbon source.

There appear to be significant limitations, however, on the usefulness of painstaking plasmid manipulation and selection procedures. A case in point is the degradation of the chlorinated phenoxyacetic acids. Although several types of plasmids appear to have evolved for the degradation of 2,4-dichlorophenoxy acetic acid ("2,4-D"), deliberate and continued searches for the isolation of microorganisms capable of utilizing 2,4,5-trichlorophenoxy acetic acid as a sole carbon source have met with failure. See, e.g., Horvath, *Bull. Environ. Contam. Toxicol.*, 5, p. 537 (1970); Rosenberg, et al., *J. Agric. Food. Chem.*, 28, p. 297 (1980); Rosenberg, et al., *J. Agric. Food. Chem.*, 28, pp. 705–709 (1980); Alexander, *Science*, 211, pp. 132–138 (1981); Don, et al., *J. Bacteriol.*, 145 pp. 681–686 (1981).

Of significant interest to the background of the present invention are prevailing scientific theories of continuous culture of microorganisms and enrichment selection.

Microbial growth is termed balanced if there is a doubling of biomass accompanied by doubling of all other properties (e.g., protein, RNA, DNA) in order to maintain a constant chemical composition. Thus microbial growth rates can be studied by studying only one biochemical component. Bacteria growing in a rich medium within a growth flask typically show a classic sigmoidal growth curve, possessing four phases, i.e., lag, exponential, stationary, and death. The closed nature of a flask with its resulting characteristic growth curve is termed a "batch" culture, since the nutrients are not renewed and hence growth remains exponential for only a few generations. Although most laboratory cultures are grown as batch cultures, microbial species in nature virtually never reach batch conditions (unlimited growth). If the growth system becomes an open system, with nutrient renewal, as well as cell and expended medium removal, then it becomes possible to maintain a microbial population in an exponential state over a long period of time. When the average value of every individual cell property remains constant over time, a "steady state" of growth and division results. This steady state is analogous to the stationary phase of batch growth and can be generated in the laboratory via continuous culture.

Typically, a bacterial culture undergoing balanced growth mimics a first order autocatalytic chemical reaction, i.e., the rate of increase at any time (t) is proportional to the number (N) of bacteria. This relationship can be expressed mathematically as, $$\log N - \log N_o = \frac{\mu}{2.303} (t - t_o)$$

wherein: $N_o$ = the number of cells at time zero; $t_o$ = time zero; and $\mu$ = the growth rate constant.

A continuous culture is a flow system in which individual cells are suspended in a (nearly) constant volume, at or near a steady state of growth established by the continual addition of fresh growth medium, and the continual removal of part of the culture. In the simples mathematical form, $$\begin{array}{c}\text{production rate of} \\ \text{cells through growth}\end{array} = \begin{array}{c}\text{cell loss rate} \\ \text{through overflow}\end{array}$$

The rate of cell loss through overflow can be stated as:

$$\frac{dN}{dt} = \frac{fN}{V_O} = [\omega] N$$

wherein:
N = number of cells
$V_O$ = culture volume (ml)
$[\omega]$ = dilution rate
f = flow rate (ml/hr)

Thus a stabilized steady culture will have $\mu = \omega$. Culture volumes have ranged from 10 ml to large scale industrial continuous culture fermentors, with dilution rates ranging from about 0.04 to 0.40 hour$^{-1}$.

Since microbial growth mimics a first order chemical reaction, it is possible to derive a relationship for the nutrient concentration effect. Curves relating growth rate to nutrient concentration are typically hyperbolic and fit the equation:

$$\mu = \mu\text{max} \frac{C}{K_s + C}$$

wherein: $\mu$ is the specific growth rate at limiting nutrient concentration (C); $\mu$ max is the growth rate at saturating concentration of nutrient; and $K_s$ is an analogous constant to the Michaelis-Menten enzyme kinetic constant, being numerically equivalent to the substrate concentration supporting a growth rate equal to $\frac{1}{2}\mu$max. As an example, values of $K_s$ for glucose and tryptophan for *Escherichia coli* are $1 \times 10^{-6}$ and $2 \times 10^{-7}$ M, respectively, or 0.18 and 0.03 $\mu$g/ml. These very low values are attributed to the high affinities characteristic of many bacterial permeases, which can be construed as an evolutionary adaptation to growth in extremely dilute solutions.

With continuous cultures, the growth rate equals the dilution rate in a stabilized system, thus $$\mu\text{max} \frac{C}{K_s + C} = \omega$$

or $$C = K_s \frac{\omega}{\mu\text{max} - \omega} = \omega$$

which states the fundamental relationship between substrate concentration (C) and dilution rate $\omega$.

Continuous culture systems can be operated either as chemostats or turbidostats. The former originated with Novick, et al., *P.N.A.S.*, 36, pp. 708–719 1950) and *Science,* 112, pp. 715–716 (1950) and with Monod, *Ann. Inst. Pasteur.*, 79, pp. 390–410 (1950), whereas the latter was first reported on by Myers, et al., *J. Gen. Physiol.*, 28, pp. 103–112 (1944). Every chemostat or turbidostat consists of four basic parts:

(1) A culture vessel (growth vessel or growth tube) in which cells are grown isolated from contamination by other organisms;
(2) A nutrient supply system that delivers sterile nutrient medium at constant flow rate, and any gases needed;
(3) A system for agitation of the culture, capable of rapid mixing of medium and gases required or produced and;
(4) A system for drainage that removes fluid from the culture vessel at the same rate as fresh medium is supplied, and allows escape of gases.

In a chemostat the flow rate is set at a particular value and growth rate of the culture adjusts to this flow rate. In contrast, a turbidostat includes an optical-sensing device, e.g., photomultiplier tube, which measures culture absorbancy or density (either by transmitted or scattered light) in the vessel; the electrical signal from this device in turn regulates the flow rate. This results in the absorbancy of the culture determining the flow rate.

Continuous culture systems traditionally have offered two valuable features for microbial study. They provide a constant source of cells in an exponential phase of growth, and they also provide for cultures to be grown at extremely low substrate concentrations, similar to environmental concentrations. Growth at low substrate concentrations has classically been used in studies on regulation of synthesis and catabolism of the limiting substrate, as well as mutant production and ecological studies.

BRIEF SUMMARY

According to the present invention, there is provided a novel procedure for generating pure and mixed cultures of microorganisms capable of dissimilating environmentally persistent chemical compounds, "plasmid-assisted molecular breeding". Microorganisms are subjected to continuously cultured growth in the presence of a source of DNA plasmids participative in dissimilation of compounds which are structurally analogous to a selected persistent compound and under chemostatic conditions including gradual increases in the concentration of the persistent compound until it constitutes a major, and preferably sole, carbon source for the organisms. One or more organisms isolated from the continuous culture provides a pure or mixed culture capable of dissimilating the persistent compound and may be employed to treat water or soil contaminated with the compound.

Target compounds for practice of plasmid-assisted molecular breeding procedures of the invention include a wide array of organic substances not usable by known microrganisms as a source of carbon. The procedures are especially applicable to developing microorganisms which dissimilate halogenated compounds and, specifically, polychlorinated aromatic compounds such as chlorinated dioxins, chlorinated phenoxyacetic acids, chlorophenols and chlorinated biphenyls.

Wild type organisms selected for growth in the plasmid-assisted molecular breeding procedures are preferably those which are capable of growth in aquatic and soil environments which are at least minimally contaminated with the target persistent compound and for which, therefore, the persistent compound is not toxic in the relatively low concentrations provided in the growth medium upon initiation of continuously cultured growth.

DNA plasmid sources useful in plasmid-assisted molecular breeding may include cells harboring plasmids, "naked" intact plasmids derived from cells, engineered plasmids subjected to amplification in cells, plasmid fragments derived from restriction endonuclease treatment of intact plasmids and plasmid fragments encapsulated in artificial membranes. Plasmids are selected on the basis of their capacity to participate in the dissimilation of compounds which are structurally analogous to but chemically or sterically simpler than the target persistent compound. As examples of plasmids useful in generating organisms capable of dissimilating persistent halogenated organic compounds there may be briefly enumerated the following: CAM, TOL (XYL), SAL, OCT, NPL (NAH), NIC, pJP1, pJP3, pUO1, pAC21, pAC25, pAC27, and pAC31.

Microorganism products of plasmid-assisted molecular breeding include mixed and, preferably, pure cultures of organisms capable of dissimilating the target persistent compound when dispersed into a soil or aqueous environment contaminated by the target compound.

Microorganism products of the invention may possess their compound dissimilative capacity as a result of the stable and transmissible incoporation of one or more discrete DNA plasmids totally or partially functional in coding for enzyme products which can degrade the persistent compound intracellularly or extracellularly. The capacity of organisms of the invention to dissimilate target compounds may also result from incorporation of selected functional DNA plasmid fragment into chromosomal material or from the combination of function of such altered chromosomes and DNA plasmids.

Specific exemplary microorganisms of the present invention include a novel *Pseudomonas cepacia* strain, A.T.C.C. No. 39027 which is capable of employing 2,4,5-trichlorophenoxyacetic acid as its sole carbon source and exhibits the capacity to oxidize a variety of related chlorinated compounds such as: 2,4-dichlorophenoxyacetic acid; 2,4,5-trichlorophenol; 2,3,5-trichlorophenol; 2,3,4,5-tetrachlorophenol; the 2,3-2,4-, 2,5-, 2,6-, 3,4- and 3,5-dichlorophenols; as well as ortho- and meta-chlorophenol.

Also exemplifying microorganism products of the invention is a mixed culture of *Arthrobacter* and *Pseudomonas* A.T.C.C. No. 39028 which can totally degrade mixtures of chlorinated biphenyls (e.g., Arochlor 1221) with release of chlorine and commensurate growth of culture components, demonstrating that degradation proceeds by other than cooxidative mechanisms.

Comprehended by the present invention are methods for diminishing the degree of contamination by specific persistent chemicals in solids, semi-solids and liquids which comprise applying thereto cultures of organisms generated by plasmid assisted molecular breeding. As an example, soil samples contaminated with varying concentrations of 2,4,5-T are essentially cleansed of contamination with the compound by culturing *P. cepacia* strain A.T.C.C. No. 39027 in the soil under conditions allowing access of the organisms to 2,4,5-T as a carbon source. Illustratively, more than 98% of 2,4,5-T (present at an initial concentration of up to 1000 μg per gram of soil) is removed from soil samples incubated for six days with about 1 to $5 \times 10^7$ cells of A.T.C.C. No. 39027 per gram of soil.

Other aspects and advantages of the present invention will become apparent upon consideration of the following detailed description thereof.

DETAILED DESCRIPTION

As employed herein, the terms "environmentally persistent chemical compound", "persistent chemical compound", "persistent compound" and "target compound" are used synonymously in the same sense as employed in the art-accepted definition of "recalcitrant molecules", i.e., "organic chemicals that endure for long periods in natural ecosystems owing to the inability of microorganisms to degrade them rapidly, if at all". See, Alexander, *Science,* 211, pp. 132–138, at p. 136 (1981). As such, the term includes both toxic and non-toxic substances (e.g., lignin) which may or may not be resistant to abiotic, non-enzymatic degradation (such as by photochemical reaction) and which may comprise single compounds or mixtures of structurally related compounds (such as mixtures of chlorinated biphenyls).

Environmentally persistent chemical compounds are, expectedly, enormously varied in their chemical constitution and their degradation may involve a wide array of chemical transformation reactions including: dehalogenation, deamination, decarboxylation, methyl oxidation, hydroxylation, ketone-formation, βoxidation, epoxide formation, nitrogen oxidation, sulfur oxidation, sulfoxide reduction, double and triple carbon-carbon bond reduction, double carbon-carbon bond hydration, and nitro, oxime, nitrile/amide metabolism. Chemical cleavage reactions which may take place during degradation of such compounds may have as substrates the following kinds of chemical bonds: ester, ether, carbon-nitrogen, peptide, carbamate, carbon-sulfur, carbon-mercury, carbon-tin, carbon-oxygen-phosphorous, phosphorous-sulfur, sulfate ester, sulfur-nitrogen and disulfide. Degradation of such compounds may also involve such conjugative chemical reactions as methylation, ether formation, N-acylation, nitration, N-nitrosation, dimerization and nitrogen heterocycle formation.

As employed herein "chemostatic conditions" shall mean and include conditions in a continuous culture of microorganisms wherein growth rate is responsive to flow rate as well as those conditions wherein flow rate is responsive to a culture's physical characteristics such as absorbancy (as in a turbidostat) or to the generation of a degradative reaction product (e.g., a halostat).

Continuous culture systems capable of providing chemostatic conditions during plasmid assisted molecular breeding may be designed in essentially classical form to provide standard, macro- and micro-sized systems. Characteristics of chemostatic continuous culture systems are exemplified in Table 1 below.

TABLE 1

Microscale Chemostat
Growth Vessel: 25 ml max (11 cm × 1.9 cm) or 10 ml max (11 cm × 1.2 cm)
Flow rate capability: 0.00011 to 798 ml/hr (ω = 0.00011–1.00)
Air Capillary size: 51 mm × 1 mm I.D.
Air Flow Rate: ca. 20–60 ml/min
Pumping System: Sage Instruments Model 341A Syringe TABLE 1-continued Pump (Cambridge, MA)
Medium Reservoir Capacity: variable 10 μl–50 ml, usually 20 ml
Macroscale Chemostat
Growth Vessel: 1–10 L
Flow Rate Range: 0–300 ml/hr (ω = 0–0.3 normal operation)
Air Flow Range: 0–16,000 ml/min (normally 10–15 ml/min)
Additional Aeration: Multiple impellor blades at 150 rpm.
Pumping Systems: Dual peristaltic pumps (input and output)
Medium Reservoir Capacity: Unlimited (usually 6 L)
Medium Scale Chemostat
Growth Vessel: 500 ml or 1000 ml
Flow Rate Range: 1.5–80 ml/hr (or 3.6–360 ml/hr) [ω = 0–0.6]
Air Flow Range: 0–250 ml/min (usually 50 ml/min)
Additional Aeration: Magnetic stirrer (50 rpm)
Pumping Systems: Manostat dual cassette pumps (or Masterflex pumps)
Medium Reservoir: Unlimited, however usually 100–1000 ml)

Large scale chemostats for practice of the invention to date were typically designed around existing fermentors (New Brunswick Scientific model MF-214-28 Microferm Fermentors, dual 15 L vessels). Impeller blade placements were adjusted to culture volume agitation of ca. 1.5 L. Additionally, the antifoam addition systems were modified to pump out spent media, cells, etc., into effluent carboys. The antifoam peristaltic pumping systems were activated by adjusting a stainless steel probe (3.2 mm O.D.) to the desired culture volume height. Nutrient supply was delivered by a modified pH controller (New Brunswick Scientific model PH 152, New Brunswick, N.J.) which allowed for variable time control between medium pumping as well as pump dwell time. Typical settings were ca. 20–45 seconds null time with 5 second pump times. This led to flow rates of ca. 10–15 ml/hr and dilution rates of ca. 0.01 with silicon tubing (either 1.6 mm I.D.×4.9 mm O.D. or 3.2 mm I.D.×4.7 mm. O.D.). All connections with the chemostats were made either with silicon tubing or glass tubing (6 mm).

Peristaltic pumps used were either Manostat cassette pumps (dual channel, 1.5–90 ml/hr, Scientific Products, McGaw Park, Ill.) or Masterflex variable speed pumps (3.6–360 ml/hr, Cole Palmer Instrument Co., Chicago, Ill.).

Anti-foaming was not ordinarily provided for as foaming is insignificant with minimal media at low cell concentrations. Wall growth of organisms in continuous culture was not of concern, and in fact was encouraged, although the effect was minimized somewhat by using spherically shaped culture vessels with the medium size chemostats (100–500 ml) which minimized the surface/volume ratio. All chemostats were operated at ambient temperature, ca. 21–23° C., although temperature controls could be provided if needed.

Air supplies were from laboratory air lines with appropriate filtration. Filtration was first through indicating drierite (500–100 ml vacuum flasks) followed by activated charcoal (6–14 mesh, Fisher Scientific, Itasca, Ill.) with the latter contained in acrylic drying units (D8160, Scientific Products, McGaw Park, Ill.) [capacity of ca. 600–700 g of 8 mesh]. Final air filtration was through autoclavable Balston DFU Grade AA filters (0.3 μm; Alltech Associates, Deerfield, Ill.).

Flow rates for both media and air were monitored with inline Gilmont F 2100 Size 11 flowmeters (1–280 ml/min air; 0.01–4 ml/min water; Scientific Products, McGaw Park, Ill.).

Selection of microorganism populations for initiation of continuous cultures in plasmid-assisted molecular breeding procedures will generally involve consideration of the target chemical and the reported capacities of known microorganisms or plasmids harbored therein to participate in degradation of structurally similar compounds. Preferably such known degradative cultures are supplemented with environmental samples derived from soil and water suspected or known to be contaminated with the target chemical. This will generally provide to the culture wild type organisms which may possess some of the genes necessary for dissimilation of the target compounds.

As an illustrative example, Table 2, below, identifies a series of environmental samples employed in initiation of continuous cultures wherein the goal was generation of microorganisms capable fo dissimilating persistent halogenated aromatic compounds.

TABLE 2

| Location | Sample Description | Persistent Chemicals |
|---|---|---|
| 1. Waukegan, Illinois | Stream bank soil, Stream sediment | PCB's |
| 2. Alkali Lake Oregon | Contaminated Desert Soil | 2,4-D, chlorophenols, dioxins |
| 3. Eglin AFB, Florida | Soil | Agent Orange, dioxins |
| 4. Love Canal, N.Y. | Spent carbon sediment, Clarifier sludge | TCDD, chlorophenols, chlorophenoxy acetic acids |
| 5. Jacksonville, Ark. | Oxidation pond sediment | Chlorophenols, dioxins |
| 6. Chicago, Illinois | Raw liquid sewage, Digester feed activated raw sewage | Unknown |

All solid or semi-solid (sludge) samples noted in Table 2 were processed similarly. Samples of about 5–10 g were transferred to phosphate ammonia salts $Cl^-$ free medium shaken vigorously, and then allowed to settle for 2–4 hours at room temperature. The upper aqueous phase was sampled for direct isolation, enrichment culture, and addition to continuous culture systems.

Direct isolation was done by plating out the supernatant onto selective plates with the tested compound as sole carbon source. Test concentrations were 200–250 $\mu$g/ml with PASK $Cl^-$ free medium and noble agar (Difco, Detroit, Mich.) at 1.25%. The PASK medium consisted of: 4.4g $K_2HPO_4$ and 1.7 g $KH_2PO_4$, 2.64 g $(NH_4)SO_4$, 0.20 g $MgSO_4$ $7H_2O$, 0.015 g $CaSO_4$ and 0.0017 g $MnSO_4$ $H_2O$ in 1.00 L of deionized water at pH 7.2. This medium was termed $Cl^-$ "free" although some chlorine ion was always present (25–50 $\mu$molar). Plates were made by separately autoclaving: a 10× solution of the phosphates and ammonium source; a 100× solution of the remaining ingredients: and noble agar in the appropriate amount of deionized water. The two stock solutions were then added to the hot water/agar solution, and the test substrate added (either from a stock solution or as a dry powder).

Enrichments were performed with PASK Cl- free medium by taking either the environmental aqueous supernatant and adding this to an enrichment bottle with 25–50 ml of medium, or by placing about 5–10 g of sample directly into an enrichment bottle with growth medium. Enrichment bottles were incubated at 30° C. and periodically sampled and plated onto the appropriate selective medium. Standard disposable petri dishes (150×10 mm) were used throughout except for dioxins, where miniplates (9×50 mm; Gelman 7232) were used in order to save substrate (5 ml to fill plate).

DNA plasmid selection for use in plasmid assisted molecular breeding procedures according to the present invention is well illustrated by the following example which is directed to the generation of a pure culture of *Pseudomonas cepacia* strain A.T.C.C. No. 39027 which is capable of employing 2,4,5-trichlorophenoxyacetic acid as a sole carbon source.

EXAMPLE 1

Microorganisms from waste dump sites and sources set out in Table 2 were inoculated into enrichment flasks with 2,4,5-T as the sole carbon source. Prolonged incubation in enrichment flasks failed to reveal any organisms capable of utilizing 2,4,5-T.

The same microorganisms were inoculated into a continuous culture operated under chemostatic conditions. Added to the culture were some *Pseudomonas putida* and *P. aeruginosa* strains harboring the degradative plasmids enumerated in Table 3, below, specifically TOL, SAL, CAM, OCT, XYL-K, pAC25, pAC27 and pAC31.

TABLE 3

| Plasmid | Degradative Pathway | Size (million daltons) | Literature Reference or Other Source |
|---|---|---|---|
| CAM | Camphor | ~300 | NRRL B-5472, 5473 (See U.S. Pat. No. 4,259,444) |
| OCT | n-Octane | ~250 | Same as above |
| SAL | Salicylate | ~40–55 | Same as above |
| NAH | Naphthalene | 46 | Same as above |
| TOL | Xylene/Toluene | 76 | Chakrabarty, Ann. Rev. Gen., 10, pp. 7–30 (1976) |
| XYL-K | Xylene/Toluene | 90 | Same as above |
| NIC | Nicotine/Nicotinate | Not Determined | Same as above |
| pJP1 | 2,4-D | 58 | Fisher, et al., J. Bacteriol., 135, pp. 798–804 (1978) |
| pJP3 | 2,4-D, 3-chlorobenzoic acid | 51 | Don, et al., J. Bacteriol., 145, pp. 681–686 (1981) |
| pUO1 | Chloroacetate | 43 | Kawasaki, et al., Agric. Biol. Chem., 45, pp. 1477–1481 (1981) |
| pAC21 | 4-Chlorobiphenyl | 65 | Kamp, et al. pp. 97–109 in "Plasmids of Medical, Environmental and Commercial Importance" Elsevier/North-Holland Biomedical Press, Amsterdam (1979) |
| pAC25 | 3-Chlorobenzoic acid | 68 | (Chatterjee, et al., J. Bacteriol., 146, pp. 639–646 (1981) (Harbored in *P. putida* strain A.T.C.C No 39029) |
| pAC27 | 4-Chlorobenzoic acid | 59 | Chatterjee, et al., pp. 519–528 in "Molecular Biology, Pathogenicity and Ecology of Bacterial Plasmids" Plenum Pub. Corp., N.Y. (1981) (Harbored in *P. aeruginosa* strain A.T.C.C. No. 39030) |

TABLE 3-continued

| Plasmid | Degradative Pathway | Size (million daltons) | Literature Reference or Other Source |
|---------|---------------------|------------------------|--------------------------------------|
| pAC31 | 3,5-Dichlorobenzoic acid | 59 | (Harbored in P. aeruginosa A.T.C.C. No. 39031) |

As may be noted from the designations of sources of plasmids set out in Table 3, all plasmids employed in the generation of P. cepacia strain A.T.C.C. No. 39027 are publicly available and/or have been deposited with the American Type Culture Collection, Rockville, MD.

The chemostat was initiated with a very low concentration of 2,4,5-T (50 µg/ml) and with relatively low concentrations (250 µg/ml) of plasmid substrates such as camphor, toluate, salicylate, chlorobenzoate, etc. Gradually the concentrations of plasmid substrates were reduced while that of 2,4,5-T was increased. Occasional administration of plasmid-harboring microorganisms was made during this period as was feedback inoculation from the output reservoir. After about 6 to 8 months, the chemostat was run with 2,4,5-T alone (500 µg/ml) as a sole source of carbon. After several weeks with 2,4,5-T as sole carbon source, the medium in the chemostat gradually turned light brown, and an increase in turbidity was visible. Continuous monitoring of the medium demonstrated appreciable loss of 2,4,5-T and release of chloride ions in the reactor medium. Streaking of the cell suspension on a nutrient agar plate demonstrated the presence of several types of colony morphologies suggesting the presence of a mixed culture. Continued subculturing with higher levels of 2,4,5-T resulted in significant reductions of growth lag and a reduction in the number of microrganism colony types, eventually revealing a single strain of P. cepacia, A.T.C.C. No. 39027.

The above example illustrates the practice of plasmid-assisted molecular breeding in the context of generating a pure culture of microorganism capable of dissimilating a single persistent compound upon continuous chemostatic culturing of numerous organisms and numerous sources of plasmids participative in dissimilation of compounds which are structurally analogous to the target compound. As illustrated by the following example, the procedure of the invention are equally applicable to generating mixed cultures of organisms which are capable of dissimilating mixtures of structurally related compounds through continuous culture under chemostatic conditions of a few selected microorganisms comprising sources of degradative plasmids.

EXAMPLE 2

By way of background, there has been no known culture of microorganisms, mixed or pure, which can utilize mono-, di- or other polychlorinated biphenyls with the release of stoichiometric amounts of chlorine. It is known, however, that many pure cultures can convert 4-chlorobiphenyl or other chlorinated biphenyls to the corresponding chlorobenzoic acids. The involvement of a plasmid specifying this conversion in a strain of K. pneumoniae has been demonstrated by co-inventor Chakrabarty and his co-workers. See, Kamp, et al. supra. Furukawa, et al. [Appl. Environ. Microbiol., 38, pp. 301–311 (1979)]described the property of a strain of Acinetobacter P6 that can utilize 30 pure isomers of chlorinated biphenyls, including several bi-, tri- and tetra-chlorobiphenyls, with the formation of corresponding chloro-benzoic acids. Subsequently, Arthrobacter strain M5 was characterized as displaying the same capability for converting chlorobiphenyls to chlorobenzoic acids. See, Furukawa, et al., Agric. Biol. Chem., pp. 1577–1583 (1979). Both strains can grow well with non-chlorinated biphenyl as a sole source of carbon and both demonstrate the presence of a 50 megadalton plasmid having an identical EcoRI restriction endonuclease profile.

As previously noted in the context of Example 1, there exists a plasmid pAC31 (harbored in P. aeruginosa strain A.T.C.C. No. 39031) which is capable of paricipation in the degradation of 3,5-dichlorobenzoic acid ("3,5-Dcb").

A preliminary study was conducted to determine the capacity for utilization of 3,5-dichlorobiphenyl ("3,5-DCB") by resting cells of Arthrobacter strain M5, a 3,5-Dcb+Pseudomonas putida strain harboring plasmid pAC31 and a mixture of the two cultures. Resting cells of the strains were incubated with 3,5-DCB (2.5 mM) at 30° C. on a shaker. At 0, 20 and 40 hours, samples were taken for determination of 3,5-DCB and 3,5-Dcb by gas chromatography. Chloride release was measured by ion selective chloride electrode. The experimental results of this study are set forth in Table 4 below.

TABLE 4

| Bacterial Strain | Incubation Time (hr.) | (mM) 3,5-DCB Consumed | (mM) 3,5-Dcb Formed | Chloride Released (%) |
|------------------|----------------------|-----------------------|---------------------|------------------------|
| P. putida (3,5-Dcb+) | 0 | 0 | 0 | 0 |
|  | 20 | 0.02 | 0 | 0 |
|  | 40 | 0.05 | 0 | 0 |
| Arthrobacter M5 | 0 | 0 | 0 | 0 |
|  | 20 | 1.8 | 2.0 | 1.5 |
|  | 40 | 2.4 | 2.4 | 2.0 |
| P. putida (3,5-Dcb+) and | 0 | 0 | 0 | 0 |
| Arthrobacter M5 | 20 | 2.4 | 0.20 | 90 |
|  | 40 | 2.48 | 0.1 | 98 |

As indicated in Table 4, the Pseudomonas and Arthrobacter strains cannot dechlorinate the dichlorobiphenyl, although the Arthrobacter strain can convert it stoichiometrically to the intermediate 3,5-Dcb compound. The presence of the 3,5-Dcb degradative plasmid pAC31 in the Pseudomonas strain appeared to allow for total degradation of the compound and stoichiometric release of chlorine.

The mixed culture was subjected to further treatment in a continuous culture under chemostatic conditions of gradual increase in concentration of a commercial mixture of polychlorinated biphenyls comprising about 21 percent chlorine (Arochlor 1221). This process has allowed the isolation of a mixed culture, A.T.C.C. No. 39028, which is capable of total dissimilation of Arochlor 1221 with chlorine release and commensurate growth of the culture in the absence of any other carbon source.

Practice of plasmid-assisted molecular breeding procedures of the present invention can result in generation of organisms with dissimilative capacities beyond those specifically correlated to the target compound employed in continuous culture under chemostatic conditions. This advantage was well exemplified by substrate veal that a single organism in the culture may emerge for degradation of Arochlor 1221.

Numerous modifications and variations of the invention as above described are expected to occur to those skilled in the art. As one example, the plasmid-assisted molecular breeding procedures of Examples 1 and 2 involved isolation of pure and mixed microorganism cultures from continuous cultures operated under chemostatic conditions and wherein the concentration of target compounds was increased until it comprised the sole carbon source. It will be understood that the gradual increases in concentration of target compound need not persist to this extent. Procedures wherein target compound is increased in concentration until it comprises a major potential carbon source (i.e., greater than 50% and up to 70%, 80%, 90% or 95% of carbon made available to the culture) may also provide useful pure and mixed cultures. Further, it is within the contemplation of the invention that plasmid assisted molecular breeding procedures may involve use of radiation and chemical mutagenesis procedures during chemostatic selection to augment development of novel microorganisms.

As another example, the foregoing description illustrates the use of microorganisms of the invention as an inoculant for soil contaminated with a specific toxic persistent compound which served as the target compound during plasmid-assisted molecular breeding of the organisms. It should be apparent, first, that all type of solids, semi-solids and liquids which are contaminated with the target compound may be advantageously treated by application of the organism thereto so long as the application procedure allows access of the microorganisms to the persistent compound as a carbon source. Next, it will be clear that microorganisms of the invention may be well suited for biological treatment of soil and water contaminated by toxic compounds other than a specific compound employed in plasmid assisted molecular breeding of the organisms. Finally, pure and mixed cultures of the invention may be employed as a single biological component of a complex system (e.g., an activated sludge system) in the treatment of a contaminated material including many persistent compounds of diverse chemical constitution.

What is claimed is:

1. *Pseudomonas cepacia* strain A.T.C.C. 39027.
2. A mixed culture of Pseudomonas and Arthrobacter, A.T.C.C. No. 39028.

* * * * *

UNITED STATES PATENT AND TRADEMARK OFFICE
CERTIFICATE OF CORRECTION

PATENT NO. : 4,535,061

DATED : August 13, 1985

INVENTOR(S) : ANANDA M. CHAKRABARTY and SCOTT T. KELLOGG

It is certified that error appears in the above-identified patent and that said Letters Patent is hereby corrected as shown below:

Column 5, line 61, change "microrganisms" to --microorganisms--.

Column 7, line 50, change "microrganisms" to --microorganisms--.

Column 9, line 21, change "fo" to --of--.

Column 13, line 11, change "concentraiton" to --concentration--.

Column 14, line 29, change "82" to --$\mu$--.

Signed and Sealed this

Sixteenth Day of December, 1986

Attest:

DONALD J. QUIGG

Attesting Officer     Commissioner of Patents and Trademarks

UNITED STATES PATENT AND TRADEMARK OFFICE
CERTIFICATE OF CORRECTION

PATENT NO. : 4,535,061

DATED : August 13, 1985

INVENTOR(S) : Ananda M. Chakrabarty and Scott T. Kellogg

It is certified that error appears in the above-identified patent and that said Letters Patent is hereby corrected as shown below:

On the title page, in the Abstract:

At line 15, delete "39027" and substitute --53876-- therefor.

At column 6, line 43, delete "39027" and substitute --53876 (deposited with the American Type Culture Collection, 12301 Parklawn Drive, Rockville, Maryland on January 27, 1989)-- therefor.

At column 6, line 67, delete "39027" and substitute --53876-- therefor.

At column 7, line 5, delete "39027" and substitute --53876-- therefor.

At column 10, line 33, delete "39027" and substitute --53876-- therefor.

At column 11, line 9, delete "39027" and substitute --53876-- therefor.

At column 11, line 35, delete "39027" and substitute --53876-- therefor.

At column 13, line 2, delete "39027" and substitute -- 53876-- therefor.

UNITED STATES PATENT AND TRADEMARK OFFICE
CERTIFICATE OF CORRECTION

PATENT NO. : 4,535,061

DATED : August 13, 1985

INVENTOR(S) : Ananda M. Chakrabarty and Scott T. Kellogg

It is certified that error appears in the above-identified patent and that said Letters Patent is hereby corrected as shown below:

At column 13, line 58, delete "39027" and substitute --53876-- therefor.

At column 14, line 16, delete "39027" and substitute --53876-- therefor.

At column 14, line 58, delete "39027" and substitute --53876-- therefor.

Signed and Sealed this

Fifth Day of February, 1991

Attest:

*Attesting Officer*

HARRY F. MANBECK, JR.

*Commissioner of Patents and Trademarks*

UNITED STATES PATENT AND TRADEMARK OFFICE
CERTIFICATE OF CORRECTION

PATENT NO. : 4,535,061                                         Page 1 of 2

DATED : August 13, 1985

INVENTOR(S) : Ananda M. Chakrabarty & Scott T. Kellogg

It is certified that error appears in the above-identified patent and that said Letters Patent is hereby corrected as shown below:

On the title page, in the Abstract

At line 15, delete 39027 and substitute --53867-- therefor.

At column 6, line 43, delete 39027 and substitute --53867 (deposited with the American Type Culture Collection, 12301 Parklawn Drive, Rockville, Maryland on January 27, 1989)-- therefor.

At column 6, line 67 delete 39027 and substitute --53867-- therefor.

At column 7, line 5, delete 39027 and substitute --53867-- therefor.

At column 10, line 33, delete 39027 and substitute --53867-- therefor.

At column 11, line 9, delete 39027 and substitute --53867-- therefor.

At column 11, line 35, delete 39027 and substitute --53867-- therefor.

At column 13, line 2, delete 39027 and substitute --53867-- therefor.

At column 13, line 58, delete 39027 and substitute --53867-- therefor.

At column 14, line 16, delete 39027 and substitute --53867-- therefor.

UNITED STATES PATENT AND TRADEMARK OFFICE
CERTIFICATE OF CORRECTION

PATENT NO. : 4,535,061

DATED : August 13, 1985

INVENTOR(S) : Ananda M. Chakrabarty & Scott T. Kellogg

It is certified that error appears in the above-identified patent and that said Letters Patent is hereby corrected as shown below:

At column 14, line 58, delete 39027 and substitute --53867-- therefor.

At column 16, line 22, delete 39027 and substitute --53867-- therefor.

This Certificate of Correction supersedes Certificate of Correction Issued February 5, 1991.

Signed and Sealed this

Sixteenth Day of November, 1993

*Attest:*

BRUCE LEHMAN

*Attesting Officer*   *Commissioner of Patents and Trademarks*